United States Patent
Braun et al.

(10) Patent No.: US 8,981,116 B2
(45) Date of Patent: Mar. 17, 2015

(54) PROCESS FOR THE PREPARATION OF ESTERS OF 1-SUBSTITUTED-3-FLUOROALKYL-PYRAZOLE-4-CARBOXYLIC ACIDS

(75) Inventors: Max Josef Braun, Wedemark (DE); Janis Jaunzems, Hannover (DE)

(73) Assignee: Solvay SA, Brussels (BE)

( * ) Notice: Subject to any disclaimer, the term of this patent is extended or adjusted under 35 U.S.C. 154(b) by 61 days.

(21) Appl. No.: 13/810,626

(22) PCT Filed: Jul. 22, 2011

(86) PCT No.: PCT/EP2011/062635
§ 371 (c)(1),
(2), (4) Date: Jan. 18, 2013

(87) PCT Pub. No.: WO2012/010692
PCT Pub. Date: Jan. 26, 2012

(65) Prior Publication Data
US 2013/0123510 A1    May 16, 2013

(30) Foreign Application Priority Data
Jul. 23, 2010  (EP) .................................... 10170633

(51) Int. Cl.
*C07D 231/14*    (2006.01)
(52) U.S. Cl.
CPC .................................. *C07D 231/14* (2013.01)
USPC ...................................................... 548/374.1
(58) Field of Classification Search
None
See application file for complete search history.

(56) References Cited

U.S. PATENT DOCUMENTS

| | | | |
|---|---|---|---|
| 5,223,526 A | 6/1993 | McLoughlin et al. | |
| 5,498,624 A | 3/1996 | McLoughlin et al. | |
| 7,501,527 B2 | 3/2009 | Lantzsch et al. | |
| 2008/0108686 A1 | 5/2008 | Gewehr et al. | |
| 2008/0153707 A1 | 6/2008 | Gewehr et al. | |
| 2008/0154045 A1 | 6/2008 | Aihara et al. | |
| 2010/0069646 A1 | 3/2010 | Sukopp et al. | |

FOREIGN PATENT DOCUMENTS

| | | | |
|---|---|---|---|
| EP | 0278945 A2 | 8/1988 | |
| EP | 1170275 A2 | 1/2002 | |
| EP | 1580189 A1 | 9/2005 | |
| JP | 4-114754 B2 | 7/2008 | |
| WO | WO 9311117 A1 | 6/1993 | |
| WO | WO 2005044804 A1 | 5/2005 | |
| WO | WO 2006066871 A1 | 6/2006 | |
| WO | WO 2006087343 A1 | 8/2006 | |
| WO | WO 2008006540 A1 | 1/2008 | |
| WO | WO 2008053043 A1 | 5/2008 | |
| WO | WO 2009021987 A1 | 2/2009 | |
| WO | WO 2009106619 A1 | 9/2009 | |
| WO | WO 2012025469 A1 | 3/2012 | |
| WO | WO 2012055864 A1 | 5/2012 | |

OTHER PUBLICATIONS

U.S. Appl. No. 13/881,366, Max Josef Braun, filed Apr. 24, 2013.
Hegde, S. G., et al —"Synthesis and Herbicidal Activity of 5-(Haloalkyl)-Substituted Thiazolo[4,5-b]pyridine-3(2H)-acetic Acid Derivatives", 1993, Journal of Agricultural and Food Chemistry, vol. 41, Issue No. 11, pp. 2131-2134, XP-002266944; 4 pgs.
Jones, Reuben G., "The Synthesis of Ethyl Ethoxymethyleneoxalacetate and Related Compounds", 1951, J. Am. Chem. Soc., vol. 73, Issue No. 8, pp. 3684-3686; 3 pgs.

*Primary Examiner* — Kamal Saeed

(57) ABSTRACT

A process for the manufacture of an ester or the respective free acid of a 1-substituted-3-fluoroalkyl-pyrazole-4-carboxylic acid of formula (I), wherein in such formula (I), Y is H, F or an alkyl group having from 1 to 12 carbon atoms which is optionally substituted by at least one halogen atom, an aralkyl group or an aryl group; $R_1$ is H or an organic residue; $R_2$ is H or an organic residue. Such process comprises submitting a compound of formula (II) to a reduction reaction, wherein in such formula (II), Y is the same as defined for formula (I); X is Cl, Br or I; $R_1'$ is H or an organic residue; and $R_2'$ is H or an organic residue.

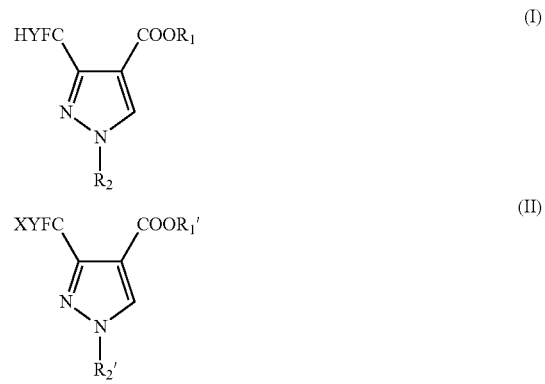

19 Claims, No Drawings

PROCESS FOR THE PREPARATION OF ESTERS OF 1-SUBSTITUTED-3-FLUOROALKYL-PYRAZOLE-4-CARBOXYLIC ACIDS

CROSS-REFERENCE TO RELATED APPLICATIONS

The present application is a U.S. national stage entry under 35 U.S.C. §371 of International Application No. PCT/EP2011/062635 filed Jul. 22, 2011, which claims priority benefit to European application no. 10170633.1 filed on Jul. 23, 2010, the whole content of this application being herein incorporated by reference for all purposes.

The invention concerns a process for the manufacture of esters of 1-substituted-3-fluoroalkyl-pyrazole-4-carboxylic acid, in particular esters of 3-difluoromethyl-1-methyl-1H-pyrazole-4-carboxylic acid, which are useful e.g. as intermediates for pharmaceuticals and agrochemicals. Moreover, the invention also relates to a process for the synthesis of substituted 3-chloro fluoroalkyl-pyrazole-4-carboxylic acid esters, in particular esters of 3-chlorofluoromethyl-1-methyl-1H-pyrazole-4-carboxylic acid.

U.S. Pat. No. 5,498,624 describes the preparation of 3-difluoromethyl-1-methyl-1H-pyrazole-4-carboxylic acid derivatives which are intermediates for the manufacture of pyrazole carboxanilide fungicides.

WO 2008/053043 discloses a process for the synthesis of difluoromethyl-substituted-pyrazole-4-carboxylic acid esters. The synthesis is carried out by reacting 4,4,4-trihalogen-substituted acetoacetic ester derivatives with chlorosilanes in the presence of magnesium or other metals of the 1st, 2nd, 3rd, 4th or 12th group of the Periodic Table of the Elements and subsequent reaction of the reaction product with a hydrazine or hydrazine derivative.

It is an object of the present invention to provide a process for the synthesis of esters of 1-substituted-3-fluoroalkyl-pyrazole-4-carboxylic acid which allows for high efficiency, and, in particular, high selectivity and for an environmental beneficial process. The process according to the invention also allows the utilization of starting materials (e.g. chlorodifluoroacetyl chloride (CDFAC)) which are available in industrial scale.

The invention consequently relates to a process for the manufacture of an ester of a 1-substituted-3-fluoroalkyl-pyrazole-4-carboxylic acid of formula (I)

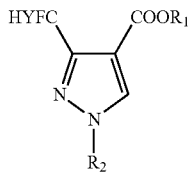

(I)

wherein
Y is H, F or an alkyl group having from 1 to 12 carbon atoms which is optionally substituted by at least one halogen atom, an aralkyl group or an aryl group;
$R_1$ is H or an organic residue,
$R_2$ is H or an organic residue, which comprises submitting a compound of formula (II)

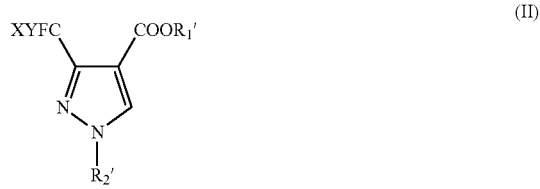

(II)

wherein Y is as defined above
X is Cl, Br or I,
$R_1'$ is H or an organic residue,
$R_2'$ is H or an organic residue,
to a reduction reaction.

The term "ester" includes, for the sake of simplicity, the free acid. The esters are preferred.

It should be noted that $R_1'$ can be identical to or different from $R_1$. Also $R_2'$ can be identical to or different from $R_2$. $R_1'$ and/or $R_2'$ are different from $R_1$ and $R_2$, if $R_1'$ and/or $R_2'$ undergo a reduction reaction in the process according to the invention. If reduction of the $R_1'$ and/or $R_2'$ occurs, the resulting $R_1$ and $R_2$ can be defined as the reduced groups of $R_1'$ and/or $R_2'$ respectively.

The term "organic residue" is intended to denote in particular linear or branched alkyl or alkylene groups which may contain hetero atoms, such as in particular boron, silicon, nitrogen, oxygen or sulphur atoms and halogen atoms, cycloalkyl groups or cycloalkylene groups, heterocycles and aromatic systems. The organic residue may contain double or triple bonds and functional groups.

The organic residue comprises at least 1 carbon atom. It often comprises at least 2 carbon atoms. It preferably comprises at least 3 carbon atoms. More particularly preferably, it comprises at least 5 carbon atoms.

The organic residue generally comprises at most 100 carbon atoms. It often comprises at most 50 carbon atoms. It preferably comprises at most 40 carbon atoms. More particularly preferably, it comprises at most 30 carbon atoms.

$R_1$ is typically selected from the group consisting of H, linear or branched alkyl or alkylene groups, cycloalkyl or cycloalkylene groups, heterocycles and aromatic systems, optionally containing heteroatoms, double bonds, triple bonds, functional groups and mixtures thereof.

$R_2$ is usually selected from the group consisting of H, linear or branched alkyl or alkylene groups, cycloalkyl or cycloalkylene groups, heterocycles and aromatic systems, optionally containing heteroatoms, double bonds, triple bonds, functional groups and mixtures thereof.

$R_1'$ is generally selected from the group consisting of H, linear or branched alkyl or alkylene groups, cycloalkyl or cycloalkylene groups, heterocycles and aromatic systems, optionally containing heteroatoms, double bonds, triple bonds, functional groups and mixtures thereof.

$R_2'$ is most often selected from the group consisting of H, linear or branched alkyl or alkylene groups, cycloalkyl or cycloalkylene groups, heterocycles and aromatic systems, optionally containing heteroatoms, double bonds, triple bonds, functional groups and mixtures thereof.

The term "alkyl group" as given in the definition of organic residue is intended to denote in particular a linear or branched alkyl substituent comprising from 1 to 20 carbon atoms, preferably 1, 2, 3, 4, 5, 6, 7, 8, 9 or 10 carbon atoms. Specific examples of such substituents are methyl, ethyl, n-propyl, isopropyl, n-butyl, isobutyl, tert-butyl, n-pentyl, isopentyl, n-hexyl, 2-hexyl, n-heptyl, n-octyl and benzyl.

The term "cycloalkyl group" is intended to denote in particular a substituent comprising at least one saturated carbocycle containing 3 to 10 carbon atoms, preferably 5, 6 or 7 carbon atoms. Specific examples of such substituents are cyclopropyl, cyclobutyl, cyclopentyl, cyclohexyl and cycloheptyl.

The term "alkylene group" or "cycloalkylene group" is intended to denote in particular the divalent radicals derived from the alkyl or cycloalkyl groups as defined above.

When the organic residue contains one or optionally more double bonds, it is often chosen from an alkenyl group comprising from 2 to 20 carbon atoms, preferably 2, 3, 4, 5, 6, 7, 8, 9 or 10 carbon atoms or a cycloalkenyl group comprising from 3 to 20 carbon atoms, preferably 3, 4, 5, 6, 7, 8, 9 or 10 carbon atoms. Specific examples of such groups are vinyl, 1-allyl, 2-allyl, n-but-2-enyl, isobutenyl, 1,3-butadienyl, cyclopentenyl, cyclohexenyl and styryl.

When the organic residue contains one or optionally more triple bonds, it is often chosen from an alkinyl group comprising from 2 to 20 carbon atoms, preferably 2, 3, 4, 5, 6, 7, 8, 9 or 10 carbon atoms. Specific examples of such groups are ethinyl, 1-propinyl, 2-propinyl, n-but-2-inyl and 2-phenylethinyl.

When the organic residue contains one or optionally more aromatic systems, it is often an aryl group comprising from 6 to 24 carbon atoms, preferably from 6 to 12 carbon atoms. Specific examples of such groups are phenyl, 1-tolyl, 2-tolyl, 3-tolyl, xylyl, 1-naphthyl and 2-naphthyl.

The term "heterocycle" is intended to denote in particular a cyclic system comprising at least one saturated or unsaturated ring made up of 3, 4, 5, 6, 7 or 8 atoms, at least one of which is a hetero atom. The hetero atom is often chosen from B, N, O, Si, P and S. It is more often chosen from N, O and S.

Specific examples of such heterocycles are aziridine, azetidine, pyrrolidine, piperidine, morpholine, 1,2,3,4-tetrahydroquinoline, 1,2,3,4-tetrahydroisoquinoline, perhydroquinoline, perhydroisoquinoline, isoxazolidine, pyrazoline, imidazoline, thiazoline, tetrahydrofuran, tetrahydrothiophene, pyran, tetrahydropyran and dioxane.

The organic residues as defined above may be unsubstituted or substituted with functional groups. The term "functional group" is intended to denote in particular a substituent comprising or consisting of a hetero atom. The hetero atom is often chosen from B, N, O, Al, Si, P, S, Sn, As and Se and the halogens. It is more often chosen from N, O, S and P, in particular N, O and S.

The functional group generally comprises 1, 2, 3, 4, 5 or 6 atoms.

By way of functional groups, mention may, for example, be made of halogens, a hydroxyl group, an alkoxy group, a mercapto group, an amino group, a nitro group, a carbonyl group, an acyl group, an optionally esterified carboxyl group, a carboxamide group, a urea group, a urethane group and the thiol derivatives of the abovementioned groups containing a carbonyl group, phosphine, phosphonate or phosphate groups, a sulphoxide group, a sulphone group and a sulphonate group.

In a preferred embodiment of the process according to the invention, $R_1$ is H, $C_1$-$C_8$-alkyl, $C_3$-$C_8$-cycloalkyl, $C_3$-$C_8$-cycloalkoxy-$C_1$-$C_4$-alkyl, $C_2$-$C_8$-alkenyl or is benzyl which is optionally substituted by 1, 2 or 3 substituents $R^{y1}$ independently of one another selected from the group consisting of $C_1$-$C_4$-alkyl, $C_1$-$C_4$-alkoxy and nitro; and $R_2$ is hydrogen, $C_1$-$C_4$-alkyl, benzyl or phenyl, where the two last-mentioned substituents may be unsubstituted or optionally substituted by 1,2 or 3 substituents $R^{y2}$ independently of one another selected from the group consisting of halogen, nitrile, nitro, $C_1$-$C_4$-alkyl, $C_1$-$C_4$-alkoxy and $C_1$-$C_4$-haloalkoxy; and X is Cl.

The terms, used in the definition of the variables, for organic groups, such as, for example, the term "halogen", are collective terms representing the individual members of these groups of organic moieties.

The prefix $C_x$-$C_y$ denotes the number of possible carbon atoms in the case in question. $C_1$-$C_4$-Alkyl includes, for example, methyl, ethyl, propyl, 1-methylethyl, butyl, 1-methylpropyl, 2-methylpropyl or 1,1-dimethylethyl.

The term "halogen" denotes in each case fluorine, bromine, chlorine or iodine, especially fluorine, chlorine or bromine.

The term "$C_1$-$C_4$-alkoxy-$C_1$-$C_4$-alkyl", as used herein, describes $C_1$-$C_4$-alkyl radicals where one carbon atom is attached to a $C_1$-$C_4$-alkoxy radical. Examples of these are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

The term "$C_2$-$C_8$-alkenyl", as used herein, describes straight-chain and branched unsaturated hydrocarbon radicals having 2 to 8 carbon atoms and at least one carbon-carbon double bond, such as, for example, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1- butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, 1-heptenyl, 2-heptenyl, 1-octenyl or 2-octenyl.

In a preferred embodiment of the process according to the invention, $R_1$ is H, $C_1$-$C_4$-alkyl or benzyl, in particular methyl, ethyl, n-propyl or isopropyl; $R_1$ is especially ethyl; and $R_2$ is H or $C_1$-$C_4$-alkyl. $R_2$ is especially methyl; X is Cl and Y is F.

In the process according to the invention, the reduction reaction of the compound of formula (II) can be carried out according to different reduction reactions.

The reduction process according to the invention can comprise reacting the compound of formula (II) with reducing agents such as $LiAlH_4$, $NaBH_4$, diisobutylaluminium hydride (DIBAH), or phosphines, including $PH_3$, trialylphosphines (example: triisopropylphosphine) and triarylphosphines (example: triphenylphosphine).

In a first embodiment, the reduction process according to the invention comprises reacting the compound of formula (II) with zinc in the presence of an alcohol. For example, the reaction can be performed as described in WO 2005/085173 with metallic zinc. An alcohol is suitably employed as proton source. In one particular aspect, the alcohol is used as solvent for the reaction with zinc. In another particular aspect, a mixture of alcohol and water is used as solvent for the reaction.

In a second and preferred embodiment, the reduction process according to the invention is a hydrogenation reaction comprising reacting the compound of formula (II) with hydrogen, in particular hydrogen gas in the presence of a hydrogenation catalyst. The use of hydrogen for said reduction reaction advantageously avoids the formation of waste.

Surprisingly, it has been found that said hydrogenation is particularly suitable for selectively substituting halogen, in particular chlorine atom, by a hydrogen atom while the pyrazole ring remains substantially unaffected.

In this second embodiment of the process according to the invention, the hydrogenation reaction is preferably carried out in the liquid phase. In this case, the compound of formula (II) is advantageously dissolved in a solvent. Solvents which can be used in the hydrogenation reaction are chosen, for example, from polar solvents. In general, polar solvents comprising at least one OH group are highly suitable. Examples of polar solvents comprising at least one OH group may be selected from a group consisting of aliphatic alcohols preferably comprising from 1 to 3 carbon atoms, water, organic acids such as acetic acid, aqueous solutions of acids, preferably inorganic acids. Aliphatic alcohols preferably comprising from 1 to 3 carbon atoms such as methanol, ethanol, isopropanol (IPA) and the like are preferred. Polar aprotic solvents may also be highly suitable, for instance tetrahydrofurane (THF), ethyl acetate, acetone, dimethylformamide (DMF), acetonitrile or dimethylsulfoxide (DMSO), especially THF. A single polar solvent can be used or a mixture of several polar solvents.

The hydrogenation reaction is generally carried out in the presence of a hydrogenation catalyst. The hydrogenation catalyst is advantageously chosen from the metals from Group VIII of the Periodic Table of the Elements (IUPAC 1970). Mention will be made in particular of a catalyst comprising at least one metal chosen from nickel, palladium, platinum and rhodium. A catalyst comprising nickel or palladium is preferred. Optionally, the reduction process comprises substituting halogen, in particular chlorine atom by a hydrogen and simultaneously hydrogenating of at least one of the unsaturated bonds in the substituents $R_1'$ and/or $R_2'$.

The hydrogenation catalyst is often a supported catalyst. Supports which can be used are chosen, for example, from alumina, silica, titanium dioxide, aluminium trifluoride, and carbon in particular active carbon or charcoal. A catalyst supported on active carbon gives good results. An example of a suitable catalyst comprises palladium on carbon support, often referred to as Pd/C, or palladium hydroxide on carbon support, often referred to as $Pd(OH)_2/C$. Other examples of suitable catalysts are for example palladium on alumina support ($Pd/Al_2O_3$), rhodium on alumina ($Rh/Al_2O_3$), or Raney Nickel (RaNi).

When the hydrogenation catalyst is a supported catalyst comprising a metal from Group VIII, the metal content is generally at least 0.1% by weight with respect to the total weight of the catalyst. The metal content is often greater than or equal to 1% by weight. Preferably, the metal content is greater than or equal to 5% by weight. The metal content is generally at most 50% by weight with respect to the total weight of the catalyst. Typical amounts of metal are 0.5 to 20% by weight of catalyst.

In a very particularly preferred way, the catalyst is supported palladium, preferably supported on a support as described above, preferably exhibiting a metal content as described above.

The hydrogenation catalyst is typically used in an amount of from 0.1 to 50 mol % compared to 1 mol of compound of formula (II), particularly from 0.5 to 20 mol %, more particularly from 1 to 5 mol %, for instance around 2, 3 or 4 mol %.

In the hydrogenation reaction, the temperature of the reaction is generally at least −10° C. The temperature of the reaction is often at least 0° C. Preferably, this temperature is at least 20° C., more preferably more than 25° C., most preferably at least 40° C., for instance at least 60° C. The temperature of the reaction is generally at most 160° C. The temperature of the reaction is often at most 150° C. Preferably, this temperature is at most 130° C. A temperature of at most 120° C., for instance at most 110° C., is very particularly preferred.

In the hydrogenation reaction, the pressure of the reaction is generally at least 1 bar absolute. Preferably, the pressure is at least 1.5 bar. The pressure of the hydrogenation reaction is generally at most 30 bar absolute. Preferably, the pressure is at most 20 bar. In a particularly preferred way, it is at most 15 bar. A pressure of lower than or equal to 10 bar is preferred. A pressure of about 5 bar is very particularly preferred.

In a particular embodiment, the hydrogenation reaction is carried out at a temperature from 0° C. to 150° C. and a pressure from 1 bar to 20 bar. Preferably the hydrogenation reaction is carried out at a temperature from 20° C. to 130° C. and a pressure from 1.5 bar to 10 bar. Most preferably, the hydrogenation reaction is carried out at a temperature from 40° C. to 120° C. and a pressure from 1.5 bar to 10 bar.

In the process according to the invention, use is preferably made of hydrogen gas as hydrogenation reactant. In this case, the pressure values of the hydrogenation reaction mentioned above generally correspond to the hydrogen pressure.

When use is made of hydrogen as hydrogenation reactant, the molar ratio of hydrogen to the compound of formula (II) is generally greater than or equal to 1. This ratio is generally at most 1000. Preferably, this ratio is at most 100. More preferably, this ratio is at most 10.

In the hydrogenation reaction, the concentration of the compound of formula II in the reaction medium is generally at least 5% by weight with respect to the total weight of the reaction medium. This concentration is often at least 10% by weight. Preferably, the concentration is at least 20% by weight. The concentration of the compound of formula II in the reaction medium is generally at most 50% by weight with respect to the total weight of the reaction medium.

In the process according to the invention, the reduction reaction is advantageously carried out in the presence of at least one additive, especially of an organic base, an inorganic base or a salt, more particularly an inorganic base or a salt. Organic bases are for instance amines or ammonium organic salts such as ammonia, triethylamine or ammonium formiate, ammonium acetate ($NH_4OAc$), and sodium acetate (NaOAc). Inorganic bases can for instance be selected from $K_2CO_3$, $Cs_2CO_3$, $Na_2CO_3$, $NaHCO_3$, $K_3PO_4$, NaOH, and KOH. Salts may be selected from the group consisting of chlorides, fluorides, iodides or Borax, for instance ammonium chloride ($NH_4Cl$), lithium chloride (LiCl), zinc chloride ($ZnCl_2$), ammonium fluoride ($NH_4F$), magnesium fluoride ($MgF_2$), lithium fluoride (LiF), aluminium fluoride ($AlF_3$), cesium fluoride (CsF), $CsAlF_4$, sodium iodide, or Borax ($Na_2B_4O_7.xH_2O$). In the process of the present invention, the additive may especially be selected from $K_2CO_3$, $NH_4Cl$, $NH_4F$, CsF, Borax and mixtures thereof, preferably at least CsF.

Addition of at least one of said additives may be especially advantageous, as it can lead to enhanced productivity and/or enhanced selectivity of the hydrogenation reaction. It also allows performing the reaction at lower temperature, compared to reaction in the absence of such additives.

Said additive is typically added in an amount of from 0.05 to 5 molar equivalents of compound of formula (II), often from 0.1 to 3, more often from 0.5 to 2, for instance around 1.

An especially preferred first aspect of the second embodiment of the present invention includes a hydrogenation reaction in the presence of $Pd(OH)_2$ and of at least an additive such as CsF, in particular in a polar aprotic solvent, THF being a suitable example.

An especially preferred second aspect of the second embodiment of the present invention includes a hydrogenation reaction in the presence of supported Pd, more particularly Pd/C, $Pd/TiO_2$ or $Pd/Al_2O_3$, most particularly Pd/C, optionally in the presence of at least an additive such as CsF. Especially suitable solvents for this preferred second aspect of the second embodiment of the invention are polar aprotic solvents, for instance THF.

An especially preferred third aspect of the second embodiment of the present invention includes a hydrogenation reaction in the presence of Raney Nickel in an aqueous solvent, especially $H_2O$, in the presence of a base, more preferably $NH_3$.

The process according to the invention allows avoiding with particular efficiency the saturation of the aromatic system of the pyrazole ring. The process according to the invention can be used for the manufacture of industrial amounts of esters of the 1-substituted-3-fluoroalkyl-pyrazole-4-carboxylic acid of formula (I).

According to the process of the present invention, compound of formula (I) can for example be purified by distillation, especially by vacuum distillation. Compound of formula (I) can also be purified by crystallization, for example after dissolution in warm 1,1,1,3,3-pentafluorobutane (Solkane®365 mfc) followed by addition of n-hexane and further cooling of the medium.

In the process of the present invention, it is also possible to remove by-products corresponding to $CFH_2$— compounds rather than $CF_2H$— compounds by dismutation in presence of $AlCl_3$ powder. Such a dismutation reaction can for example be performed in Solkane®365 mfc at room temperature. The reaction medium may then be washed with water to remove aluminium salts, the organic phase separated, dried for example over $Na_2SO_4$, and evaporated.

The invention also relates to a method of the manufacture of a compound of formula II

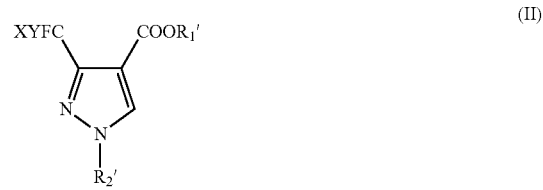

wherein
X is Cl, Br or I
Y is H, F or an alkyl group having from 1 to 12 carbon atoms which is optionally substituted by at least one halogen atom, an aralkyl group or an aryl group;
$R_1'$ is H or an organic residue
$R_2'$ is H or an organic residue which comprises the following steps
(a) producing a compound of formula (IV): XYFCC(O)$CH_2C(O)OR_1'$ (IV) wherein $R_1'$, X and Y are as defined above, by addition of a fluorine containing carboxylic acid chloride to ketene followed by esterification,
(b) adding an orthoformate of formula (III): $HC(OR_3)_3$ (III) wherein $R_3$ is $C_3$-$C_8$-cycloalkyl, $C_2$-$C_8$-alkenyl, benzyl or phenyl, to the compound of formula (IV): XYFCC(O)$CH_2C(O)OR_1$ (IV) to produce an addition product of formula (V):

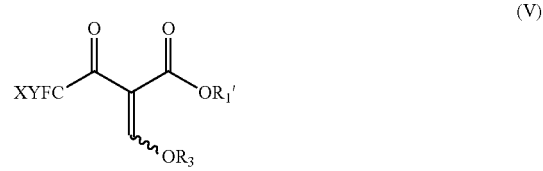

wherein $R_1'$, $R_3$, X and Y are as defined above
and
(c) reacting said addition product with a hydrazine of formula (VI):
$R_2'NHNH_2$ (VI) wherein $R_2'$ is as defined above.

The definitions and preferences described above for the compounds used in the process according to the invention equally apply to the method according to the invention.

In a preferred embodiment of the method according to the invention, $R_3$ in the orthoformate of formula (III) is selected from the group consisting of $C_1$-$C_4$-alkyl and benzyl and in particular from the group consisting of methyl, ethyl, isopropyl and benzyl. $R_3$ is especially ethyl.

It has been found, surprisingly, that the method according to the invention makes it possible to prepare the compound of formula II with high regioselectivity and with a high yield.

In step (b) of the method of the manufacture of the compound of formula II of the present invention, the addition reaction of the orthoformate of formula (III) to the compound of formula (IV) can be carried out, for example, analogously to the reaction described in WO 2008/053043.

Said addition reaction also forms an alcohol $R_3OH$. The alcohol $R_3OH$ is generally removed from the reaction equilibrium, for example in that it is distilled off or bound chemically. In the latter, for example the reaction can be carried out in the presence of an anhydride of a carboxylic acid, for example a $C_1$-$C_4$-alkanecarboxylic acid, such as acetic anhydride.

In the method according to the invention, the molar ratio of the orthoformate of formula (III) to the compound of formula (IV) preferably is from 1.1 to 5, and particularly preferably from 1.2:2 to about 2. Most preferably, the molar ratio is about 2.

In the method according to the invention, step (b) is generally carried out at a temperature from 80° C. to 180° C., preferably from 100° C. to 150° C., more preferably from 120° C. to 140° C.

If desired, the compound of formula (V) is purified prior to being used in step (c) of the method according to the invention. Examples of purification steps which can be used to purify the compound of formula (V) include removal of solvents, extraction, distillation, chromatography, or a combination of these methods. It is preferred to subject the reaction mixture obtained in step (b) of the method according to the invention to a distillation.

The method according to the invention advantageously avoids the use of expensive starting materials, in particular 2,2-difluoroacetoacetic esters instead it is possible to use the much less expensive halodifluoromethyl compounds, such as 2-chloro-2,2-difluoroacetoacetic esters. For instance, 2,2-difluoroacetoacetic esters are in general prepared by the Claissen reaction. For agrochemical applications, said Claisen reaction often needs expensive bases and leads to extensive waste formation. The preparation of the compounds of general formula (IV) in step(a) by the ketene technology allows to avoid or minimize waste formation and doesn't need an quite expensive base. According to WO-A-2009/021987, the compounds of formula (IV) can be obtained, by addition of fluorine containing carboxylic acid chlorides to ketene followed by esterification. The used raw materials, such as difluorochloroacetyl chloride are available in industrial scale and can be produced by environmentally friendly technologies such as e.g. photochemical oxidation of 1,1-difluoro-1,2,2-trichloroethane with oxygen.

Some of the compounds of formula (IV): XYFCC(O)$CH_2C(O)OR_1$ (IV), produced in step (a) of the method of the present invention are commercially available or can be prepared according to other known synthetic methods. For instance, the compounds of formula (IV) can be prepared by Claisen condensation of the corresponding fluorine containing carboxylate and acetate.

In the method according to the invention, the hydrazine of formula (VI) can be used in step (c) in anhydrous or hydrate form. The hydrazine of formula (VI) can be used for example as an anhydrous solution or an aqueous solution. Preferably, said hydrazine is in the form of an anhydrous solution.

If desired, the hydrazine of formula (VI) can be dissolved in an organic solvent, for example an organic solvent which comprises at least one halogen in such as described above in the context process of the invention.

In one aspect of the method of the present invention, the hydrazine compound (VI) in anhydrous form is added to a reaction solution comprising compound (V) and an organic solvent which comprises at least one halogen.

In another aspect of the method of the present invention, the hydrazine compound (VI) dissolved in an organic solvent, in particular the organic solvent which comprises at least one halogen, is added to the reaction solution comprising compound (V) and the organic solvent which comprises at least one halogen.

In yet another aspect of the process of the present invention, the compound (V) is added to the hydrazine compound (VI), preferably dissolved in the organic solvent which comprises at least one halogen.

In an alternative and more preferred aspect of the process of the present invention, the compound (V) present in the organic solvent which comprises at least one halogen is added to the hydrazine compound (VI), preferably dissolved in the organic solvent which comprises at least one halogen.

In the method according to the invention, the molar ratio of the hydrazine of formula (VI) to the compound of formula (V) preferably is from 0.8 to 1.2, and particularly preferably from 0.8 to 1.0 to about 1. Most preferably, the molar ratio is about 1.

In the method according to the invention, the reaction in step (c) is generally carried out in a solvent. The solvent to be used may, for example, be a protic polar solvent, a hydrocarbon, an aliphatic hydrocarbon, an aprotic polar solvent or an ionic liquid.

Examples of suitable protic polar solvents include aliphatic alcohols having preferably 1 to 4 carbon atoms, such as methanol, ethanol, n-propanol, isopropanol, n-butanol, isobutanol or tert-butanol.

Examples of suitable hydrocarbons include aromatic hydrocarbons, aliphatic hydrocarbon or halogenated hydrocarbons.

Suitable aromatic hydrocarbons are selected, for example from benzene, toluene, xylenes, cumene, chlorobenzene, nitrobenzene and tertbutylbenzene.

Suitable aliphatic hydrocarbons are selected for example from pentane, hexane or octane.

Suitable halogenated hydrocarbons are selected for example from hydrochlorocarbons such as dichloromethane, chloroform, carbon tetrachloride or 1,2-dichloroethane, or hydrofluorocarbons such as 1,1,1,3,3-pentafluorobutane (Solkane®365 mfc) or hydrochlorofluorocarbons, such as, 3,3-dichloro-1,1,1,2,2-pentafluoropropane and/or 1,3-dichloro-1,1,2,2,3-pentafluoropropane.

Examples of suitable aprotic polar solvents include ethers, amides, nitriles such as acetonitrile or propionitrile or esters such as ethyl acetate, butyl acetate or dimethyl carbonate.

Ethers may be cyclic or acyclic ethers, such as for example diethyl ether, tert-butyl methyl ether (MTBE), tetrahydrofuran (THF) or dioxane. Amides may be cyclic or acyclic, such as dimethylformamide, dimethylacetamide, N-methylpyrrolidone or tetramethylurea.

These solvents may be used alone or in combination as a mixture.

The reaction in step (c) is preferably carried out in a halogenated hydrocarbon, in particular in a hydrofluorocarbon and particularly preferably in 1,1,1,3,3-pentafluorobutane (Solkane®365 mfc). The use of a hydrofluorocarbon, in particular 1,1,1,3,3-pentafluorobutane as solvent allows for particularly efficient formation of the esters of 1-substituted-3-fluoroalkyl-pyrazole-4-carboxylic acid in very high regioselectivities.

In a preferred aspect of the method of the present invention, the solvent is substantially free of water.

For the purpose of the present invention, the term "solvent substantially free of water" denotes in particular that the content of water is equal to or lower than 1 wt % by weight relative to the total weight of solvent, preferably equal to or lower than 7000 ppm, more preferably equal to or lower than 5000 ppm, most preferably equal to or lower than 2000 ppm. The solvent substantially free of water generally contains at least 1 ppm by weight of water, often at least 10 ppm by weight of water relative to the total weight of solvent. Solvents which are substantially free of water allow to maintain a high reaction rate and the formation of phase separation and consequently, in general, no additional phase transfer catalysts are required.

If appropriate, the solvent is used usually in an amount of from 50 to 99 by weight, preferably from 60 to 99% by weight, more preferably from 75 to 99% by weight of the solvent relative to the total weight of the reaction medium.

If desired, the reaction in step (c) optionally may be carried out in the presence of a base. If a base is used, it may be an inorganic base or an organic base. When an inorganic base is used, it may be suitably selected from the group consisting of alkali metal hydroxides such as sodium hydroxide, potassium hydroxide, lithium hydroxide, cesium hydroxide, alkaline earth metal hydroxides such as calcium hydroxide, barium hydroxide, magnesium hydroxide, strontium hydroxide, and basic alkali metal salts such as sodium carbonate, sodium hydrogencarbonate, potassium carbonate and potassium hydrogencarbonate. Preferred bases are sodium hydroxide and potassium hydroxide. Most preferred base is potassium hydroxide. When an organic base is used, it may be suitably selected from the group consisting of nitrogen-containing heterocyclic compounds such as pyridine, quinoline or picoline; and tertiary bases such as triethylamine, dimethylaniline, diethylaniline and 4-dimethylaminopyridine. Among them, pyridine, triethylamine, dimethylaniline, diethylaniline and 4-dimethylaminopyridine are preferred. A single base can be used or a mixture of several bases.

In the method according to the invention, step (c) is generally carried out at a temperature from −20° C. to 60° C., preferably from 0° C. to 50° C., more preferably from 10° C. to 40° C. In a specific embodiment, an initial reaction temperature is set and the reaction temperature is changed during the reaction. Typical initial reaction temperatures range from −60 to 0° C., in particular from −60 to −20° C. Good results were obtained with the temperature set from −30 to −20° C. If appropriate, during the reaction the reaction mixture is warmed to a temperature of from 0 to 60° C., in particular from 10 to 40° C. It has been found that the compounds of formula (II) are stable to decomposition but reactive towards hydrogenation.

In a most preferred aspect of the invention described herein, the compound of formula (I) is an ester of 1-methyl-3-difluoromethyl-pyrazole-4-carboxylic acid, in particular the ethyl ester.

This compound can be obtained for example from the reduction of an ester of 1-methyl-3-chlorodifluoromethyl-pyrazole-4-carboxylic acid as compound of formula (II), in particular the ethyl ester, with hydrogen using palladium on carbon support as suitable catalyst.

In a preferred embodiment of this especially preferred process of the present invention,
(a) the 1-methyl-3-chlorodifluoromethyl-pyrazole-4-carboxylic acid as compound of formula (II), in particular the ethyl ester, is obtained from the reaction of an ester of 2-(ethoxymethylene)-4-chloro-4,4-difluoro-3-oxobutanoic acid as compound of formula (V), in particular the ethyl ester, with methylhydrazine as compound of formula (VI).
(b) said 2-(ethoxymethylene)-4-chloro-4,4-difluoro-3-oxobutanoic acid is formed by the addition reaction of an orthoformate of formula (III), in particular triethyl orthoformate, to an ester of 4-chloro-4,4-difluoro-3-oxobutanoic acid as compound of formula (IV), in particular the ethyl ester.

The invention also concerns the use of the compound of formula (I) or formula (II) in accordance with the invention as an intermediate in the manufacture of an agrochemically or pharmaceutically active compound.

The invention also concerns a process for the manufacture of an agrochemically or pharmaceutically active compound which comprises the use, the process or the method according to the invention. Particularly, the compound of formula (II) according to the invention can be (a) used as starting material in the process according to the invention to produce compound of formula (I) and (b) the compound of formula (I) is further reacted to manufacture an agrochemically or pharmaceutically active compound. An example of further reaction according to step (b) is illustrated in WO 2005/123690, the respective content of which is incorporated by reference into the present patent application.

Should the disclosure of any patents, patent applications, and publications which are incorporated herein by reference conflict with the description of the present application to the extent that it may render a term unclear, the present description shall take precedence.

The following example is intended to further explain the invention without limiting it.

Example 1

Preparation of ethyl-4,4-difluoro-4-chloro 3-oxo-butanoic acid

In a three-neck round bottom flask, chlorodifluoroacetyl chloride (148.92 g, 1 mol) was dissolved in methylene chloride (500 mL) and the solution was cooled to −30° C. During 2 hours, ketene from a ketene generator (at a rate of ca. 930 mmol/h) was passed through the solution of chlorodifluoroacetyl chloride. The reaction mixture was warmed up to 0° C. and kept for 1 hour at 0° C. Ethanol (61.98 g, 1.94 mol) was added dropwise to the solution while keeping the temperature below 5° C. The solution was stirred for another 0.5 hour. The reaction mixture was transferred to a 2-liter flask and concentrated on a rotary evaporator under reduced pressure (30° C., 300 mBar). The residue (282.78 g) was further distilled over a 60-cm Vigreux column under a pressure of 30 mBar. Ethyl-4,4-difluoro-4-chloro 3-oxo-butanoic acid was recovered at a temperature of 58-65° C. as a colorless liquid. The yield was 85% of the theoretical yield, and a purity of 98.0% was obtained.

Example 2

Preparation of ethyl 1-methyl-3-chlorodifluoromethyl-pyrazole-4-carboxylate (CDFMMP)

A solution of ethyl 4-chloro-4,4-difluoro-3-oxo-butanoate (19 g, 95 mmol), triethyl orthoformate (28 g, 190 mmol) and acetic anhydride (29 g, 284 mmol) were heated to 120 to 140° C. with continuous removal of the low boilers, like ethyl acetate produced. After 7 h the low volatility components are removed in vacuum yield more or less quantitative, although during distillation of the product variable yields are observed.

Crude ethyl 2-(ethoxymethylene)-4-chloro-4,4-difluoro-3-oxobutanoate (95 mmol) dissolved in the solvent Solkane®365 mfc (200 mL) is reacted with methylhydrazine (4.9 mL, 95 mmol) under ice cooling. GC shows a ratio of 85% CDFMMP to 15% of the regio isomer. After 1 h at room temperature the reaction mixture is washed with 2 N HCl (100 mL) and water (100 mL). After drying with sodium sulfate, filtration and concentration under reduced pressure the desired product (14 g, 64% over 2 steps) is isolated by column chromatography.

Examples 3-20

Reduction of CDFMMP to ethyl 1-methyl-3-difluoromethyl-pyrazole-4-carboxylate (DFMMP) by reduction in the presence of zinc and an alcohol The reduction of CDFMMP was carried out in an autoclave in the presence of zinc and optional additive, during 3 hours at 70° C., except examples 15-20 which were carried out during 6 hours. The experimental data are summarized in Table 1.

TABLE 1

| Ex. | Zn (mol. eq) | Solvent | Additive (mol eq.) | DFMMP yield (%) |
|---|---|---|---|---|
| 3 | 2 | EtOH | — | No reaction |
| 4 | 2 | EtOH | TFA (0.1 eq) | No reaction |
| 5 | 2 | EtOH | AcCl (0.1 eq) | No reaction |
| 6 | 2 | THF | NiCl2$^a$ (0.04 eq) | No reaction |
| 7 | 2 | Acetic acid | — | 4 |
| 8 | 2 | EtOH:H$_2$O 9:1 | NH$_4$Cl (1 eq) + PdCl$_2$ (0.1 eq) | 27 |
| 9 | 2 | EtOH:H$_2$O 9:1 | NH$_4$F (1 eq) | 52 |
| 10 | 2 | EtOH:H$_2$O 9:1 | MgF$_2$ (1 eq) | 9 |
| 11 | 2 | EtOH:H$_2$O 9:1 | LiF (1 eq) | 5 |
| 12 | 2 | EtOH:H$_2$O 9:1 | CsF (1 eq) | 82 |
| 13 | 2 | EtOH:H$_2$O 9:1 | NaI (1 eq)$^a$ | 15 |
| 14 | 2 | EtOH:H$_2$O 9:1 | CsF (1 eq) + MgF$_2$ (1 eq)$^b$ | 67 |
| 15 | 2 | EtOH:H$_2$O 9:1 | CsF (0.1 eq) | 1 |
| 16 | 2 | EtOH:H$_2$O 9:1 | CsF (0.5 eq) | 77 |
| 17 | 2 | EtOH:H$_2$O 9:1 | CsF (1.0 eq) | 97 |
| 18 | 2 | EtOH:H$_2$O 9:1 | CsF (1.5 eq) | 79 |
| 19 | 0.5 | EtOH:H$_2$O 9:1 | CsF (1.0 eq) | 15 |
| 20 | 2 | absolute EtOH | CsF (1 eq) | 1 |

The DFMMP yield was measured by GC analysis (peak %).
$^a$Reaction conducted at room temperature
$^b$Finkelstein in DMF
$^c$MgF$_2$ added after 2 hours and heated fro +4 hours

Examples 21-55

Reduction of CDFMMP to ethyl 1-methyl-3-difluoromethyl-pyrazole-4-carboxylate (DFMMP) in the Presence of Supported Pd as Hydrogenation Catalyst The reduction of CDFMMP was carried out with hydrogen in an autoclave in the presence of supported Pd catalyst and optional additives, at different temperatures, under different H$_2$ pressure and different reaction times. The experimental data are summarized in Tables 2 and 3.

As a more specific example, trial 53 was conducted as follows. 95 mg of CDFMMP (0.42 mmol) were dissolved in about 2 mL of THF. To this solution were added 64 mg of cesium fluoride (0.42 mmol), and 20 mg of Pd 10% on carbon support. The mixture was stirred in a steel reactor at 70° C. for 3 hours at 1 bar hydrogen pressure (measured by rt). The reaction medium was cooled down, solids were filtered and washed with THF, and solvent was evaporated yielding crude crystalline DFMMP. The DFMMP yield was measured by GC analysis (peak %). The selectivity to DFMMP is given by the following formula:

Selectivity (%)=DFMMP Yield (%)/[Me-MMP Yield (%)+CFH$_2$-MMP]

TABLE 2

| Ex. | Cat. | Cat. amount (mol %) | Solv. | T (° C.) | p H$_2$ (bar) | Additive (mol eq.) | t (h) | DFMMP yield (%) |
|---|---|---|---|---|---|---|---|---|
| 21 | 10% Pd/C | 1 | EtOH | 110 | 15 | — | 4 | 20 |
| 22 | 10% Pd/C | 1 | EtOH | 115 | 15 | — | 8 | 35 |
| 23 | 10% Pd/C | 1 | EtOH | 130 | 10 | — | 22 | 61$^a$ |
| 24 | 10% Pd/C | 1 | EtOH | 130 | 10 | — | 42 | 68$^a$ |
| 25 | 10% Pd/C | 1 | EtOH | RT | 10 | — | 4 | No reaction |
| 26 | 10% Pd/C | 1 | Acetic acid | RT | 10 | — | 4 | No reaction |
| 27 | 10% Pd/C | 1 | — | RT | 10 | — | 4 | No reaction |
| 28 | 10% Pd/C | 1 | EtOH | 50 | 20 | — | 4 | No reaction |
| 29 | 10% Pd/C | 1 | EtOH | 110 | 10 | Ammonium formiate | 4 | 5 |
| 30 | 10% Pd/C | 1 | EtOH | 25 | 10 | CsF (1 eq) | 4 | 49 |
| 31 | 10% Pd/C | 1 | EtOH | 50 | 10 | CsF (1 eq) | 4 | 74 |
| 32 | 10% Pd/C | 2 | EtOH | 75 | 10 | CsF (1 eq) | 4 | 72 |
| 33 | 10% Pd/C | 1 | EtOH | 75 | 10 | CsF (1 eq) | 1 | 66 |
| 34 | 10% Pd/C | 1 | EtOH | 75 | 10 | CsF (1 eq) | 4 | 73 |
| 35 | 10% Pd/C | 0.5 | EtOH | 75 | 10 | CsF (1 eq) | 4 | 59 |
| 36 | 10% Pd/C | 1 | EtOH | 75 | 10 | CsF (1 eq) | 1.5 | 68 |
| 37 | 10% Pd/C | 1 | EtOH | 90 | 10 | CsF (1 eq) | 4 | 66 |
| 38 | 10% Pd/C | 1 | EtOH | 100 | 10 | CsF (1 eq) | 4 | 68 |
| 39 | 10% Pd/C | 1 | EtOH | 110 | 10 | CsF (1 eq) | 4 | 65 |
| 40 | 10% Pd/C | 1 | EtOH | 50 | 10 | CsF (0.4 eq) | 4 | 32 |
| 41 | 10% Pd/C | 1 | EtOH | 50 | 10 | CsF (2 eq) | 4 | 61 |
| 42 | 5% Pd/C | 1 | EtOH | 75 | 10 | CsF (1 eq) | 2 | 66 |
| 43 | 20% Pd/C | 1 | EtOH | 75 | 10 | CsF (1 eq) | 2 | 73 |
| 44 | 5% Pd/C | 0.5 | EtOH | 120 | 10 | CsF (1 eq) | 4 | 66 |
| 45 | 5% Pd/C | 0.5 | EtOH | 100 | 10 | CsF (1 eq) | 4 | 66 |
| 46 | 5% Pd/C | 0.5 | EtOH | 75 | 10 | CsF (1 eq) | 4 | 27 |
| 47 | 10% Pd/C | 1 | EtOH | 75 | 10 | Borax (1 eq) | 4 | 6 |
| 48 | 10% Pd/C | 1 | EtOH | 90 | 10 | Borax (1 eq) | 4 | 12 |
| 49 | 10% Pd/C | 1 | EtOH | 100 | 10 | Borax (1 eq) | 6 | 37 |
| 50 | 10% Pd/C | 1 | EtOH | 100 | 10 | Borax (1 eq) | 4 | 70 |
| 51 | 10% Pd/C | 1 | EtOH | 110 | 10 | Borax (1 eq) | 4 | 68 |
| 52 | 20% Pd/C | 1 | EtOH | 110 | 10 | Borax (1 eq) | 4 | 79 |

$^a$traces of full reduction of CF$_2$Cl group to CH$_3$ group

TABLE 3

| Ex. | Cat. | Cat. amount (mol %) | Solv. | T (° C.) | p H$_2$ (bar) | Additive (mol eq.) | t (h) | DFMMP yield (%) | DFMMP select. (%) |
|---|---|---|---|---|---|---|---|---|---|
| 53 | 10 % Pd/C | 4.5 | THF | 70 | 1 | CsF (1 eq) | 4 | 32 | 2.86 |
| 54 | 5 % Pd/Al$_2$O$_3$ | 2.25 | THF | 110 | 10 | CsF (0.1 eq) + molecular sieve (42 wt %) + K$_2$CO$_3$ (1 eq) | 2 | 52 | 7.73 |
| 55 | 0.5 % Pd/TiO$_2$ | 0.45 | THF | 110 | 10 | CsF (0.1eq) + molecular sieve (42 wt %) + K$_2$CO$_3$ (1 eq) | 17 | 70 | 9.51 |

Examples 56-64

Reduction of CDFMMP to ethyl 1-methyl-3-difluoromethyl-pyrazole-4-carboxylate (DFMMP) in the Presence of Pd(OH)$_2$/C as Hydrogenation Catalyst The reduction of CDFMMP was carried out with hydrogen in an autoclave in the presence of Pd(OH)$_2$ 20% on carbon (Pearlman's catalyst) and optional additives, at different temperatures, under different H$_2$ pressure and different reaction times. The experimental data are summarized in Table 4.

As a more specific example, trial 62 was conducted as follows. 95 mg of CDFMMP (0.42 mmol) were dissolved in about 3 mL of THF. To this solution were added 32 mg of cesium fluoride (0.21 mmol), 40 mg of flash silica gel, 60 mg of potassium carbonate (0.43 mmol), and 20 mg of Pd(OH)$_2$ 20% on carbon support. The mixture was stirred in a steel reactor at 110° C. for 2 hours at 10 bar hydrogen pressure (measured by rt). The reaction medium was cooled down, solids were filtered and washed with THF, and solvent was evaporated yielding crude crystalline DFMMP. The DFMMP yield was measured by GC analysis (peak %). The selectivity to DFMMP is given by the following formula:

Selectivity (%)=DFMMP Yield (%)/[Me-MMP Yield (%)+CFH$_2$-MMP]

Examples 65-67

Reduction of CDFMMP to ethyl 1-methyl-3-difluoromethyl-pyrazole-4-carboxylate (DFMMP) in the Presence of Raney Nickel as Hydrogenation Catalyst The reduction of CDFMMP was carried out with hydrogen in an autoclave in the presence of Raney Nickel catalyst and optional additives, at different temperatures, under different H$_2$ pressure and different reaction times. The experimental data are summarized in Table 5.

As a more specific example, trial 67 was conducted as follows. 28 g of CDFMMP (126 mmol) were dissolved in about 200 mL water in a steel reactor. To this solution were added 1.05 g of wet Raney Nickel and 15 ml of 28% aqueous ammonia solution. The mixture was stirred (700 rpm) at 70° C. for 24 hours at 11 bar hydrogen constant pressure. The reaction medium was cooled down, extracted 2 times with solvent Solkane®365 mfc, organic phase was dried over Na$_2$SO$_4$, and was evaporated to yield DFMMP. The DFMMP yield was measured by GC analysis (peak %). The selectivity to DFMMP is given by the following formula:

Selectivity (%)=DFMMP Yield (%)/[Me-MMP Yield (%)+CFH$_2$-MMP]

TABLE 4

| Ex. | Cat. amount (mol %) | Solv. | T (° C.) | p H$_2$ (bar) | Additive (mol eq.) | t (h) | DFMMP yield (%) | DFMMP select. (%) |
|---|---|---|---|---|---|---|---|---|
| 56 | 6.8 | EtOH | 100 | 20 | — | 4 | No reaction | — |
| 57 | 6.8 | THF | 70 | 1 | CsF (1 eq) | 21 | 32 | 1.78 |
| 58 | 6.8 | THF | 110 | 5 | CsF (1 eq) | 4 | 83 | 4.88 |
| 59 | 6.8 | THF | 110 | 10 | CsF (1 eq) | 2 | 36 | 7.20 |
| 60 | 6.8 | THF | 70 | 1 | Cs$_2$CO$_3$ (1 eq) | 3 | 53 | 2.04 |
| 61 | 13.6 | THF | 110 | 10 | CsF (1 eq) + AlF$_3$ (1.1 eq) | 2 | 69 | 4.10 |
| 62 | 6.8 | THF | 110 | 10 | CsF (0.5 eq) + silicagel (40 mg) + K$_2$CO$_3$ (1 eq) | 2 | 86 | 6.67 |
| 63 | 6.8 | THF + H$_2$O (1:2) | 110 | 10 | CsF (0.1) | 2 | 71 | 7.5 |
| 64 | 6.8 | H2O + 365* (5:3) | 110 | 10 | — | 2 | 78 | 7.27 |

*365 = 1,1,1,3,3-pentafluorobutane (Solkane ® 365 mfc)

TABLE 5

| Ex. | Cat. amount (mol %) | Solv. | T (° C.) | p H$_2$ (bar) | Additive (mol eq.) | t (h) | DFMMP yield (%) | DFMMP select. (%) |
|---|---|---|---|---|---|---|---|---|
| 65 | 81 | H$_2$O | 110 | 10 | NH$_3$ (1 eq) + NH$_4$F (1 eq) | 0.5 | 79 | 4.03 |
| 66 | 40.5 | H$_2$O | 110 | 10 | NH$_3$ (1 eq) | 0.5 | 80 | 4.18 |
| 67 | 14 | H$_2$O | 70 | 11 | NH$_3$ (1 eq) | 24 | 91 | 12.49 |

Examples 68-70

Reduction of CDFMMP to ethyl 1-methyl-3-difluoromethyl-pyrazole-4-carboxylate (DFMMP) in the Presence of Rh/Al$_2$O$_3$ as Hydrogenation Catalyst The reduction of CDFMMP was carried out with hydrogen in an autoclave in the presence of Rh/Al$_2$O$_3$ catalyst and optional additives, at different temperatures, under different H$_2$ pressure and different reaction times. The experimental data are summarized in Table 6.

As a more specific example, trial 68 was conducted as follows. 95 mg of CDFMMP (0.42 mmol) were dissolved in about 2 mL of EtOH. To this solution were added 64 mg of cesium fluoride (0.42 mmol), and 90 mg of Rh 5% on alumina support. The mixture was stirred in a steel reactor at 80° C. for 20 hours at 1 bar hydrogen pressure (measured by rt). The DFMMP yield was measured by GC analysis (peak %). The selectivity to DFMMP is given by the following formula:

Selectivity (%)=DFMMP Yield (%)/[Me-MMP Yield (%)+CFH$_2$-MMP]

TABLE 6

| Ex. | Cat. amount (mol %) | Solv. | T (° C.) | p H$_2$ (bar) | Additive (mol eq.) | t (h) | DFMMP yield (%) | DFMMP select. (%) |
|---|---|---|---|---|---|---|---|---|
| 68 | 10.4 | EtOH | 80 | 1 | CsF (1 eq) | 20 | 21 | 5.52 |
| 69 | 5.8 | EtOH | 110 | 5 | CsF (1 eq) | 24 | 31 | 4.42 |
| 70 | 4.6 | THF | 110 | 10 | CsF (1 eq) + molecular sieve (40 mg) | 5 | 31 | 10.70 |

The invention claimed is:

1. A process for the manufacture of an ester of a 1-substituted-3-fluoroalkyl-pyrazole-4-carboxylic acid of formula (I)

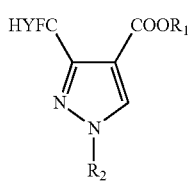

wherein

Y is H, F or an alkyl group having from 1 to 12 carbon atoms which is optionally substituted by at least one halogen atom, an aralkyl group or an aryl group, R$_1$ is H or an organic residue, R$_2$ is H or an organic residue, said process comprising submitting a compound of formula (II) to a reduction reaction,

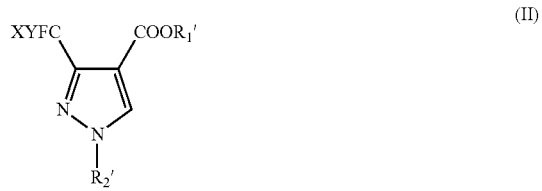

wherein:

Y is the same as defined above for formula (I),

X is Cl, Br or I,

R$_1$' is H or an organic residue, and

R$_2$' is H or an organic residue.

2. The process according to claim 1, wherein R$_1$ is methyl, ethyl, n-propyl or isopropyl.

3. The process according to claim 1, wherein R$_2$ is methyl.

4. The process according to claim 1, wherein X is Cl; and wherein Y is F.

5. The process according to claim 1, wherein the reduction is carried out with hydrogen in the presence of a hydrogenation catalyst selected from the group consisting of metals from Group VIII of the Periodic Table of the Elements.

6. The process according to claim 5, wherein the catalyst is a supported catalyst with a support selected from the group consisting of alumina, silica, and carbon.

7. The process according to claim 1, wherein the temperature of the reaction is from −10° C. to 150° C.

8. The process according to claim 1, wherein the pressure of the reaction is from 1 bar absolute to 30 bar absolute; and wherein the molar ratio of hydrogen to a compound of formula (II) is from 1 to 1000.

9. The process according to claim 1, wherein the reduction reaction is conducted in the presence of at least one additive selected from the group consisting of K$_2$CO$_3$, NH$_4$Cl, NH$_4$F, CsF, and Borax.

10. A method for the manufacture of a compound of formula II

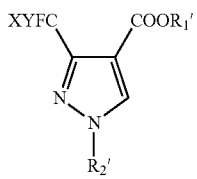

wherein
X is Cl, Br or I,
Y is H, F or an alkyl group having from 1 to 12 carbon atoms which is optionally substituted by at least one halogen atom, an aralkyl group or an aryl group,
R₁' is H or an organic residue,
R₂' is H or an organic residue,
said method comprising the following steps
(a) producing a compound of formula (IV): XYFCC(O)CH₂C(O)OR₁' (IV) wherein R₁', X and Y are the same as defined above for formula (II), by addition of a fluorine containing carboxylic acid chloride to ketene followed by esterification;
(b) adding an orthoformate of formula (III): HC(OR₃)₃ (III) wherein R₃ is selected from the group consisting of C₁-C₈-alkyl, C₃-C₈-cycloalkyl, C₂-C₈-alkenyl, benzyl, and phenyl, to the compound of formula (IV): XYFCC(O)CH₂C(O)OR₁' (IV) to produce an addition product of formula (V):

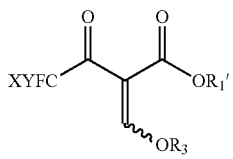

wherein R₁', R₃, X, and Y are the same as defined above; and
(c) reacting said addition product of formula (V) with a hydrazine of formula (VI):
R₂'NHNH₂ (VI), wherein R₂' is the same as defined above.

11. The method according to claim 10, wherein X is Cl; and wherein Y is F.

12. The method according to claim 10, wherein the reaction in step (b) is carried out in a hydrofluorocarbon solvent.

13. The process according to claim 1, wherein the compound of formula (II) is obtained according to a method comprising the following steps:
a) producing a compound of formula (IV): XYFCC(O)CH₂C(O)OR₁' (IV) wherein R₁', X and Y are the same as defined for formula (II), by addition of a fluorine containing carboxylic acid chloride to ketene followed by esterification;
(b) adding an orthoformate of formula (III): HC(OR₃)₃ (III) wherein R₃ is selected from the group consisting of C₁-C₈-alkyl, C₃-C₈-cycloalkyl, C₂-C₈-alkenyl, benzyl, and phenyl, to the compound of formula (IV): XYFCC(O)CH₂C(O)OR₁' (IV) to produce an addition product of formula (V):

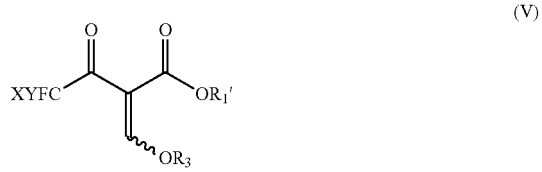

wherein R₁', R₃, X, and Y are the same as defined above; and
(c) reacting said addition product of formula (V) with a hydrazine of formula (VI):
R₂'NHNH₂ (VI), wherein R₂' is as defined above.

14. A process for the manufacture of an agrochemically or pharmaceutically active compound which comprises using a compound of formula (I) as an intermediate,

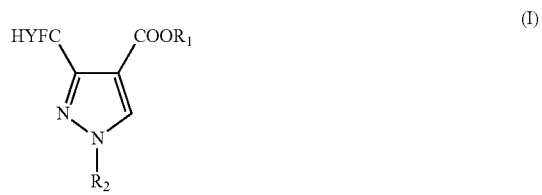

wherein:
Y is H, F or an alkyl group having from 1 to 12 carbon atoms which is optionally substituted by at least one halogen atom, an aralkyl group or an aryl group,
R₁ is H or an organic residue, and
R₂ is H or an organic residue.

15. The process according to claim 14, wherein R₁ is methyl, ethyl, n-propyl, or isopropyl; wherein R₂ is methyl; wherein X is Cl; and wherein Y is F.

16. The process according to claim 2, wherein R₂ is methyl.

17. The process according to claim 5, wherein said hydrogenation catalyst is selected from the group consisting of nickel, palladium, platinum and rhodium.

18. The process according to claim 5, wherein said hydrogenation catalyst is selected from the group consisting of Raney nickel and palladium.

19. The process according to claim 5, wherein said hydrogenation catalyst is a supported palladium catalyst selected from the group consisting of palladium on carbon support (Pd/C) and palladium hydroxide on carbon support (Pd(OH)₂/C).

* * * * *